US011946017B2

(12) United States Patent
Bärz et al.

(10) Patent No.: US 11,946,017 B2
(45) Date of Patent: Apr. 2, 2024

(54) METHOD OF SEPARATING LIPIDS FROM A LYSED LIPIDS CONTAINING BIOMASS

(71) Applicants: Evonik Operations GmbH, Essen (DE); DSM IP Assets B.V., Heerlen (NL)

(72) Inventors: Manfred Bärz, Freigericht (DE); Marc Beiser, Nidda (DE); Georg Borchers, Bad Nauheim (DE); Stephen Robert Cherinko, Georgetown, SC (US); Mathias Dernedde, Bruchköbel (DE); Michael Diehl, Frankfurt (DE); Xiao Daniel Dong, Woodstock, MD (US); Jürgen Haberland, Haltern am See (DE); Michael Benjamin Johnson, Baltimore, MD (US); Robert Cody Kertis, Timmonsville, SC (US); Jochen Lebert, Glattbach (DE); Neil Francis Leininger, Winchester, KY (US); Kirt Lyvell Matthews, Sr., Fort Mill, SC (US); Holger Pfeifer, Hanau (DE); Christian Rabe, Grossostheim (DE); Shannon Elizabeth Ethier Resop, Olney, MD (US); Ginger Marie Shank, Winchester, KY (US); Vinod Tarwade, Ellicott City, MD (US); David Allen Tinsley, Versailles, KY (US); Daniel Verkoeijen, Florence, SC (US)

(73) Assignees: Evonik Operations GmbH, Essen (DE); DSM IP Assets B.V., Te Heerlen (NL)

( * ) Notice: Subject to any disclaimer, the term of this patent is extended or adjusted under 35 U.S.C. 154(b) by 0 days.

(21) Appl. No.: 16/317,305

(22) PCT Filed: Jul. 12, 2017

(86) PCT No.: PCT/EP2017/067585
§ 371 (c)(1),
(2) Date: Jan. 11, 2019

(87) PCT Pub. No.: WO2018/011286
PCT Pub. Date: Jan. 18, 2018

(65) Prior Publication Data
US 2020/0231898 A1    Jul. 23, 2020

Related U.S. Application Data

(60) Provisional application No. 62/361,805, filed on Jul. 13, 2016.

(30) Foreign Application Priority Data

Sep. 16, 2016  (EP) .................... 16189213

(51) Int. Cl.
*C11B 1/12* (2006.01)
*A23K 10/12* (2016.01)
*A23K 20/158* (2016.01)
*C11B 1/02* (2006.01)

(52) U.S. Cl.
CPC ............... *C11B 1/12* (2013.01); *A23K 10/12* (2016.05); *A23K 20/158* (2016.05); *C11B 1/025* (2013.01)

(58) Field of Classification Search
CPC .. C01B 1/12; C01B 1/14; A23K 10/12; A23K 20/158
See application file for complete search history.

(56) References Cited

U.S. PATENT DOCUMENTS

| | | |
|---|---|---|
| 5,583,019 A | 12/1996 | Barclay |
| 5,622,710 A * | 4/1997 | Binder ................. A23K 20/142 424/438 |
| 6,166,230 A | 12/2000 | Bijl et al. |
| 6,166,231 A | 12/2000 | Hoeksema |
| 6,255,505 B1 | 7/2001 | Bijl et al. |
| 6,410,281 B1 | 6/2002 | Barclay |
| 6,410,282 B1 | 6/2002 | Kumar et al. |
| 6,441,208 B2 | 8/2002 | Bijl et al. |
| 6,727,373 B2 | 4/2004 | Bijl et al. |
| 6,750,048 B2 | 6/2004 | Ruecker et al. |
| 6,977,167 B2 | 12/2005 | Barclay |
| 7,005,280 B2 | 2/2006 | Barclay |
| 7,011,962 B2 | 3/2006 | Barclay |
| 7,041,485 B2 | 4/2006 | Bouarab et al. |
| 7,163,811 B2 | 1/2007 | Behrens et al. |
| 7,252,979 B2 | 8/2007 | Behrens et al. |
| 7,351,558 B2 | 4/2008 | Ruecker et al. |
| 7,419,596 B2 | 9/2008 | Dueppen et al. |

(Continued)

FOREIGN PATENT DOCUMENTS

| | | |
|---|---|---|
| AU | 2011226731 | 9/2011 |
| EP | 1 178 118 | 2/2017 |

(Continued)

OTHER PUBLICATIONS

International Search Report for corresponding international application PCT/EP2017/067585, filed Jul. 12, 2017.
Written Opinion of the International Searching Authority for corresponding international application PCT/ EP2017/067585, filed Jul. 12, 2017.
International Preliminary Report on Patentability for corresponding international application PCT/EP2017/067585, filed Jul. 12, 2017.
International Search Report for PCT/EP2017/067570, filed Jul. 12, 2017; for copending U.S. Appl. No. 16/317,249.

(Continued)

*Primary Examiner* — Yong L Chu
(74) *Attorney, Agent, or Firm* — Law Office of: Michael A. Sanzo, LLC

(57) ABSTRACT

The current invention relates to a method of separating polyunsaturated fatty acids containing lipids from a lipids containing biomass.

13 Claims, No Drawings

(56) References Cited

U.S. PATENT DOCUMENTS

| | | | |
|---|---|---|---|
| 7,431,952 B2 | 10/2008 | Bijl et al. |
| 7,470,527 B2 | 12/2008 | Streekstra et al. |
| 7,566,570 B2 | 7/2009 | Abril |
| 7,579,174 B2 | 8/2009 | Bailey et al. |
| 7,662,598 B2 | 2/2010 | Ruecker et al. |
| 7,732,170 B2 | 6/2010 | Bailey et al. |
| 7,776,375 B2 | 8/2010 | Bertholet et al. |
| 7,781,193 B2 | 8/2010 | Ruecker et al. |
| 7,968,737 B2 | 6/2011 | Kawashima et al. |
| 8,217,151 B2 | 7/2012 | Schaap et al. |
| 8,415,506 B2 | 4/2013 | Waibel et al. |
| 9,023,625 B2 | 5/2015 | Pottathil et al. |
| 9,045,785 B2 | 6/2015 | Pfeifer, III |
| 9,896,642 B2 | 2/2018 | Wittenberg et al. |
| 10,342,772 B2 | 7/2019 | Barker et al. |
| 10,364,207 B2 | 7/2019 | Barker et al. |
| 10,472,316 B2 | 11/2019 | McClements et al. |
| 10,531,679 B2 | 1/2020 | Rudinger et al. |
| 10,619,175 B2 | 4/2020 | Rabe et al. |
| 10,842,174 B2 | 11/2020 | Durhuus et al. |
| 11,124,736 B2 | 9/2021 | Triplett et al. |
| 11,261,400 B2 | 3/2022 | Bahl et al. |
| 11,324,234 B2 | 5/2022 | Silva et al. |
| 11,352,651 B2 | 6/2022 | Diehl et al. |
| 11,414,621 B2 | 8/2022 | Heining et al. |
| 11,542,220 B2 | 1/2023 | Heining et al. |
| 2003/0143659 A1 | 7/2003 | Bijl et al. |
| 2007/0003686 A1 | 1/2007 | Fichtali et al. |
| 2008/0032360 A1 | 2/2008 | Bailey et al. |
| 2008/0032365 A1 | 2/2008 | Bailey et al. |
| 2008/0166780 A1 | 7/2008 | Barclay |
| 2008/0199923 A1 | 8/2008 | Barclay |
| 2008/0233239 A1 | 9/2008 | Avramis et al. |
| 2008/0305531 A1 | 12/2008 | Lam et al. |
| 2009/0326267 A1 | 12/2009 | Bijl et al. |
| 2010/0227042 A1 | 9/2010 | Penet et al. |
| 2011/0091947 A1 | 4/2011 | Kim et al. |
| 2011/0098356 A1 | 4/2011 | Leininger et al. |
| 2011/0124034 A1 | 5/2011 | Kuehnle et al. |
| 2011/0201683 A1 | 8/2011 | Bezelgues et al. |
| 2011/0295028 A1 | 12/2011 | Cherinko et al. |
| 2012/0016145 A1 | 1/2012 | D'Addario et al. |
| 2012/0059180 A1 | 3/2012 | Dueppen et al. |
| 2013/0065282 A1 | 3/2013 | Tran et al. |
| 2013/0102802 A1 | 4/2013 | Sathish et al. |
| 2013/0172590 A1 | 7/2013 | Pfeifer, III |
| 2014/0096437 A1 | 4/2014 | Crowell et al. |
| 2015/0104557 A1 | 4/2015 | Rusing et al. |
| 2015/0176042 A1 | 6/2015 | Dennis et al. |
| 2016/0052846 A1 | 2/2016 | Gooding et al. |
| 2016/0183565 A1 | 6/2016 | Rudinger et al. |
| 2016/0249642 A1 | 9/2016 | Rabe et al. |
| 2016/0249643 A1 | 9/2016 | Rabe et al. |
| 2016/0289592 A1 | 10/2016 | Massetti et al. |
| 2016/0319218 A1 | 11/2016 | Leininger et al. |
| 2017/0137742 A1 | 5/2017 | Heiska et al. |
| 2017/0290356 A1 | 10/2017 | Silva et al. |
| 2017/0295823 A1 | 10/2017 | Rabe et al. |
| 2017/0295824 A1 | 10/2017 | Priefert et al. |
| 2017/0298318 A1 | 10/2017 | Rabe et al. |
| 2017/0303561 A1 | 10/2017 | Durhuus et al. |
| 2017/0306365 A1 | 10/2017 | Rabe et al. |
| 2018/0071658 A1 | 3/2018 | Hale et al. |
| 2018/0192669 A1 | 7/2018 | Wilson |
| 2018/0200644 A1 | 7/2018 | Lewis |
| 2019/0249108 A1 | 8/2019 | Cherinko |
| 2019/0300818 A1* | 10/2019 | Barz ............... C12P 7/6427 |
| 2019/0323043 A1* | 10/2019 | Diehl ............... C11B 1/10 |
| 2019/0390135 A1 | 12/2019 | Leininger et al. |
| 2020/0015500 A1 | 1/2020 | De Vriendt |
| 2020/0231896 A1 | 7/2020 | Bahl et al. |
| 2020/0339498 A1 | 10/2020 | Heining et al. |
| 2020/0362373 A1 | 11/2020 | Leininger et al. |
| 2020/0383353 A1 | 12/2020 | Wilson et al. |
| 2020/0404938 A1 | 12/2020 | Heining et al. |
| 2021/0017467 A1 | 1/2021 | Adugna et al. |
| 2021/0024966 A1 | 1/2021 | Heining et al. |
| 2021/0163842 A1 | 6/2021 | Heining et al. |
| 2021/0171991 A1 | 6/2021 | Burja et al. |
| 2021/0207056 A1 | 7/2021 | Heining et al. |
| 2021/0386095 A1 | 12/2021 | Erickson et al. |
| 2022/0017929 A1 | 1/2022 | Priefert et al. |
| 2022/0017930 A1 | 1/2022 | Priefert et al. |
| 2023/0242836 A1 | 8/2023 | Diehl et al. |

FOREIGN PATENT DOCUMENTS

| | | | |
|---|---|---|---|
| EP | 1 252 324 | 10/2020 | |
| JP | H08 275793 | 10/1996 | |
| SU | 1446142 | 12/1988 | |
| WO | WO 91/07498 | 4/1991 | |
| WO | WO 94/08467 | 4/1994 | |
| WO | WO 97/36996 | 10/1997 | |
| WO | WO 97/37032 | 10/1997 | |
| WO | WO 01/53512 | 7/2001 | |
| WO | WO 01/54510 | 8/2001 | |
| WO | WO 2011/153246 | 12/2011 | |
| WO | WO 2012/109642 | 8/2012 | |
| WO | WO 2014/122087 | 8/2014 | |
| WO | WO 2014/122092 | 8/2014 | |
| WO | WO 2015/059696 | 6/2015 | |
| WO | WO 2015/095688 | 6/2015 | |
| WO | WO 2015/095693 | 6/2015 | |
| WO | WO 2015/095694 | 6/2015 | |
| WO | WO-2015095688 A1 * | 6/2015 | ............ C11B 1/025 |
| WO | WO-2015095696 A1 * | 6/2015 | ............ C07C 51/42 |
| WO | WO 2018/011275 | 1/2018 | |
| WO | WO 2018/011283 | 1/2018 | |
| WO | WO 2018/013670 | 1/2018 | |
| WO | WO 2018/122057 | 7/2018 | |
| WO | WO 2019/032880 | 2/2019 | |
| WO | WO 2019/048327 | 3/2019 | |
| WO | WO 2019/063669 | 4/2019 | |
| WO | WO 2019/121752 | 6/2019 | |
| WO | WO 2019/122030 | 6/2019 | |
| WO | WO 2019/122031 | 6/2019 | |
| WO | WO 2019/191544 | 10/2019 | |
| WO | WO 2019/191545 | 10/2019 | |
| WO | WO 2019/219396 | 11/2019 | |
| WO | WO 2019/219443 | 11/2019 | |
| WO | WO 2020/036814 | 2/2020 | |
| WO | WO 2020/094750 | 5/2020 | |
| WO | WO 2020/094751 | 5/2020 | |
| WO | WO 2020/109472 | 6/2020 | |
| WO | WO 2020/123965 | 6/2020 | |

OTHER PUBLICATIONS

Written Opinion of the International Searching Authority for PCT/EP2017/067570, filed Jul. 12, 2017; for copending U.S. Appl. No. 16/317,249.

International Preliminary Report on Patentability for PCT/EP2017/067570, filed Jul. 12, 2017; for copending U.S. Appl. No. 16/317,249.

U.S. Appl. No. 16/317,249, filed Jan. 11, 2019, Barz.

Office Action for copending U.S. Appl. No. 16/473,805, dated May 28, 2020.

Restriction Requirement for copending U.S. Appl. No. 16/317,249, dated Jun. 24, 2020.

International Preliminary Report on Patentability for international application PCT/EP2018/073323 filed Aug. 30, 2018, corresponding to copending U.S. Appl. No. 16/644,443.

U.S. Appl. No. 15/315,094, filed Nov. 30, 2016, US-2018/0192669 A1, Jul. 12, 2018, Wilson.

U.S. Appl. No. 16/309,632, filed Dec. 13, 2018, US-2019/0249108 A1, Aug. 15, 2019, Cherinko.

International Search Report for PCT/EP2018/073323, filed Aug. 30, 2018; for copending U.S. Appl. No. 16/644,443.

Written Opinion of the International Searching Authority PCT/EP2018/073323, filed Aug. 30, 2018; for copending U.S. Appl. No. 16/644,443.

U.S. Appl. No. 16/639,529, filed Feb. 14, 2020, Burja.

U.S. Appl. No. 16/644,443, filed Mar. 4, 2020, Bahl.

(56) References Cited

OTHER PUBLICATIONS

International Search Report for PCT/EP2017/083712, filed Dec. 20, 2017; for copending U.S. Appl. No. 16/473,805.
Written Opinion of the International Searching Authority for PCT/EP2017/083712, filed Dec. 20, 2017; for copending U.S. Appl. No. 16/473,805.
International Preliminary Report on Patentability for PCT/EP2017/083712, filed Dec. 20, 2017; for copending U.S. Appl. No. 16/473,805.
European Search Report and Search Opinion for European application EP 17 15 8286, filed Feb. 28, 2017; for counterpart of copending U.S. Appl. No. 16/473,805.
U.S. Appl. No. 14/904,665, filed Jan. 12, 2016, US-2016/0183565 A1, Jun. 30, 2016, Rudinger.
U.S. Appl. No. 15/027,429, filed Apr. 5, 2016, US-2016/0249642 A1, Sep. 1, 2016, Rabe.
U.S. Appl. No. 15/516,022, filed Mar. 31, 2017, US-2017/0295823 A1, Oct. 19, 2017, Rabe.
U.S. Appl. No. 15/516,023, filed Mar. 31, 2017, US-2017/0290356 A1, Oct. 12, 2017, Silva.
U.S. Appl. No. 15/516,024, filed Mar. 31, 2017, US-2017/0295824 A1, Oct. 19, 2017, Priefert.
U.S. Appl. No. 15/516,038, filed Mar. 31, 2017, US-2017/0298318 A1, Oct. 19, 2017, Rabe.
U.S. Appl. No. 15/516,044, filed Mar. 31, 2017,US-2017/0306365 A1, Oct. 26, 2017, Rabe.
U.S. Appl. No. 15/516,058, filed Mar. 31, 2017,US-2017/0303561 A1, Oct. 26, 2017, Durhuus.
U.S. Appl. No. 16/473,805, filed Jun. 26, 2019, Diehl.
European Search Report and Search Opinion for European application EP 17 19 6348 filed Oct. 13, 2017; counterpart of copending U.S. Appl. No. 16/644,443.
International Search Report for PCT/EP2018/085606, filed Dec. 18, 2018; for copending U.S. Appl. No. 16/956,453.
Written Opinion of the International Searching Authority for PCT/EP2018/085606, filed Dec. 18, 2018; for copending U.S. Appl. No. 16/956,453.
International Preliminary Report on Patentability for PCT/EP2018/085606, filed Dec. 18, 2018; for copending U.S. Appl. No. 16/956,453.
European Search Report and Search Opinion for European application EP 18 15 6840 filed Feb. 15, 2018, counterpart of copending U.S. Appl. No. 16/956,453.
International Search Report for PCT/EP2019/061244 filed May 2, 2019, for copending U.S. Appl. No. 17/055,083.
Written Opinion of the International Searching Authority for PCT/EP2019/061244 filed May 2, 2019, for copending U.S. Appl. No. 17/055,083.
International Preliminary Report on Patentability for PCT/EP2019/061244 filed May 2, 2019, for copending U.S. Appl. No. 17/055,083.
International Search Report for PCT/EP2019/061629 filed May 7, 2019, for copending U.S. Appl. No. 17/055,047.
Written Opinion of the International Searching Authority for PCT/EP2019/061629 filed May 7, 2019, for copending U.S. Appl. No. 17/055,047.
International Preliminary Report on Patentability for PCT/EP2019/061629 filed May 7, 2019, for copending U.S. Appl. No. 17/055,047.
Hu, et al., " A review of recent developments of pre-treatment technologies and hydrothermal liquefaction of microalgae for bio-crude oil production," *Renewable and Sustainable Energy Reviews* 101:476-492 (2019).
U.S. Appl. No. 16/956,453, filed Jun. 19, 2020, US-2020/0339498 A1, Oct. 29, 2020, Heining.
U.S. Appl. No. 17/055,047, filed Nov. 12, 2020, Heining.
U.S. Appl. No. 17/055,083, filed Nov. 12, 2020, Heining.
Saien, et al., "Effect of aqueous phase pH on liquid-liquid extraction with impinging-jets contacting technique," *Journal of Industrial and Engineering Chemistry* 16:1001-1005 (2010).
Final Office Action for copending application U.S. Appl. No. 16/473,805, dated Feb. 10, 2021.
Restriction Requirement for copending application U.S. Appl. No. 16/644,443, dated Dec. 21, 2021.
Response to Restriction Requirement for copending application U.S. Appl. No. 16/644,443, filed Feb. 21, 2021.
Non Final Office Action for copending application U.S. Appl. No. 16/644,443, dated Apr. 26, 2021.
Amendment & Response to Non Final Office Action for copending application U.S. Appl. No. 16/317,249, filed May 7, 2021.
Restriction Requirement for copending U.S. Appl. No. 16/956,453, ated May 20, 2021.
Request for Continued Examination for copending U.S. Appl. No. 16/473,805, filed Jun. 10, 2021.
Amendment & Response to Accompany Request for Continued Examination for copending U.S. Appl. No. 16/473,805, filed Jun. 10, 2021.
Response to Restriction Requirement for copending U.S. Appl. No. 16/956,453, filed Jul. 14, 2021.
Final Office Action for copending U.S. Appl. No. 16/317,249, dated Aug. 26, 2021.
CFSTR (Continuous Flow Stirred Tank Reactor, Chapter 8, Sec. 2, pp. 1-2, published online Dec. 2010) (Year 2010).
U.S. Appl. No. 16/469,286, filed Jun. 13, 2019, US-2020/0015500 A1, Jan. 16, 2020, De Vriendt.
U.S. Appl. No. 16/636,940, filed Feb. 6, 2020, US-2020/0362373 A1, Nov. 19, 2020, Leininger.
U.S. Appl. No. 16/886,691, filed May 28, 2020, US-2020/0383353 A1, Dec. 10, 2020, Wilson.
U.S. Appl. No. 16/956,820, filed Jun. 22, 2020, US-2020/0404938 A1, Dec. 31, 2020, Heining.
U.S. Appl. No. 17/042,788, filed Sep. 28, 2020, US-2021/0024966 A1, Jan. 28, 2021, Heining.
U.S. Appl. No. 17/042,791, filed Sep. 28, 2020, US-2021/0017467 A1, Jan. 21, 2021, Adugna.
U.S. Appl. No. 17/284,463, filed Apr. 10, 2021, Erickson.
U.S. Appl. No. 17/291,608, filed May 6, 2021, Priefert.
U.S. Appl. No. 17/291,610, filed May 6, 2021, Priefert.
Non Final Office Action for copending U.S. Appl. No. 16/956,453, dated Aug. 2, 2021.
Request for Continued Examination for copending U.S. Appl. No. 16/473,249, filed Nov. 30, 2021.
Amendment & Response to Accompany Request for Continued Examination for copending U.S. Appl. No. 16/473,249, filed Nov. 30, 2021.
Response to Non Final Office Action for copending U.S. Appl. No. 16/956,453, filed Dec. 2, 2021.
Non Final Office Action for copending U.S. Appl. No. 17/055,047, dated Dec. 16, 2021.
Amendment & Response to Non Final Office Action for copending U.S. Appl. No. 17/055,047, filed Jan. 20, 2022.
Non Final Office Action for copending U.S. Appl. No. 16/956,453, dated Feb. 8, 2022.
Non Final Office Action for copending U.S. Appl. No. 16/317,249, dated Mar. 24, 2022.
Notice of Allowance for copending U.S. Appl. No. 17/055,047, dated Mar. 28, 2022.
Amendment & Response to Non Final Office Action for copending U.S. Appl. No. 16/956,453, filed Jun. 22, 2022.
Amendment & Response to Non Final Office Action for copending U.S. Appl. No. 16/317,249, filed Jun. 22, 2022.
Final Office Action for copending U.S. Appl. No. 16/317,249, dated Oct. 5, 2022.
Notice of Allowance for copending U.S. Appl. No. 16/956,453, dated Sep. 1, 2022.
Request for Continued Examination for copending U.S. Appl. No. 16/317,249, filed Feb. 3, 2023.
Amendment & Response for copending U.S. Appl. No. 16/317,249, filed Feb. 3, 2023.
Non Final Office Action for copending U.S. Appl. No. 16/317,249, dated Mar. 31, 2023.
Amendment & Response for copending U.S. Appl. No. 16/317,249, filed May 8, 2023.
U.S. Appl. No. 18/010,795, filed Dec. 15, 2022, Diehl.
Non Final Office Action for copending U.S. Appl. No. 17/055,083 dated Aug. 3, 2023.

(56) References Cited

OTHER PUBLICATIONS

Amendment & Response for copending U.S. Appl. No. 17/055,083, filed Nov. 1, 2023.
Response to Restriction Requirement for copending U.S. Appl. No. 16/317,249, filed Aug. 24, 2020.
Response to Office Action for copending U.S. Appl. No. 16/473,805, filed Aug. 28, 2020.
Non Final Office Action for copending U.S. Appl. No. 16/317,249, dated Dec. 7, 2020.

* cited by examiner

METHOD OF SEPARATING LIPIDS FROM A LYSED LIPIDS CONTAINING BIOMASS

Cross Reference to Related Applications

The present application is US national stage of international application PCT/EP2017/067585, which has an international filing date of Jul. 12, 2017, and which was published in English on Jan. 18, 2018. The application claims the benefit of US provisional application 62/361,805, filed on Jul. 13, 2016 and priority to European application 16189213.8, filed on Sep. 16, 2016. The contents of these prior applications is hereby incorporated by reference in their entirety.

The current invention relates to a method of separating polyunsaturated fatty acids containing lipids from a lipids containing biomass.

PUFAs (polyunsaturated fatty acids) containing lipids are of high interest in the feed, food and pharmaceutical industry. Due to overfishing there is a high need for alternative sources for PUFAs containing lipids besides fish oil. It turned out that besides certain yeast and algal strains in particular microalgal cells like those of the order Thraustochytriales are a very good source for PUFAs containing lipids.

But with respect to microbial organisms and in particular cells of the order Thraustochytriales, which produce the PUFAs containing lipids, the isolation of the oil from the cells turned out as a particular problem. The most effective way of isolating the oil was the use of organic solvents like hexane. But the use of organic solvents leads to hazardous operating conditions, requires the use of expensive explosion-proof equipment and requires the implementation of an expensive solvent recovery process to avoid pollution of the environment.

In the attempt to avoid the use of organic solvents, as an effective alternative way for isolating the oil has turned out the salting-out of the oil with high amounts of sodium chloride. But the use of high amounts of sodium chloride leads to a delipidated biomass by-product which due to the high salt content cannot be utilized as a feed ingredient, so that the process is not very sustainable. Further, the high salt concentration leads to fast corrosion of the used steel equipment.

Thus, it was the object of the current invention to provide an effective method for isolating a lipid, in particular a PUFAs containing lipid, from lipids containing cells, in particular of the order Thraustochytriales, and simultaneously avoiding not only the need of organic solvents, but further avoid the need of high amounts of salts for realizing the effective isolation of the oil from the cells.

It was a further object of the current invention to provide a method for isolating a lipid, in particular a PUFAs containing lipid, from lipids containing cells, in particular of the order Thraustochytriales, and simultaneously providing a delipidated biomass which can be utilized in a commercial way, preferably in the agricultural field.

It turned out that an effective separation of the lipid from the cell debris containing aqueous phase can be realized, if the lysed cell mixture is incubated at a low alkaline pH and a temperature of not more than 100° C. for a time period of at least 10 hours. By keeping the temperature below 100° C., it was possible to prohibit at least essentially saponification of the fatty acid esters.

Thus, a first subject of the current invention is a method of separating a polyunsaturated fatty acids (PUFAs) containing lipid from the debris of a biomass, comprising the following steps:
a) Providing a suspension of a biomass comprising cells which contain a PUFAs containing lipid;
b) Lysing the cells of the biomass;
c) Heating the suspension as obtained in step (b) to a temperature of of 80° C. to 100° C., preferably 85° C. to 95° C., more preferably about 90° C., while adjusting the pH to a value of 9.5 to 11.5, preferably 10.0 to 11.0, more preferably 10.3 to 10.7;
d) Keeping the temperature and pH value in the ranges as depicted in (c) for at least 10 hours, preferably 15 to 40 hours, more preferably 20 to 36 hours.

The steps (c) and (d) lead to the separation of the oil containing light phase and the water, cell debris, salts and residual oil containing heavy phase, as obtained by lysing the cells of the biomass. This separation of the light and heavy phase is also called "de-emulsification" or "demulsification" in the context of this application.

The order of the measures in step (d) is of no importance. Adjusting of the temperature can be carried out before or after adjusting the pH value.

Preferably, in the steps (b), (c) and (d) of the method the suspension is continuously mixed by using a stirrer and/or an agitator. In the method steps (c) and/or (d) preferably low shear agitation and/or axial-flow agitation is applied, in particular as disclosed in WO 2015/095694. Impellers suitable for agitating prior and during steps (c) and/or (d) include in particular straight blade impellers, Rushton blade impellers, axial flow impellers, radial flow impellers, concave blade disc impellers, high-efficiency impellers, propellers, paddles, turbines and combinations thereof.

Lysing of the cells of the biomass can be carried out by methods as known to those skilled in the art, in particular enzymatically, mechanically, physically, or chemically, or by applying combinations thereof.

Depending on the time of exposure and/or the degree of force applied, a composition comprising only lysed cells or a composition comprising a mixture of cell debris and intact cells may be obtained. The term "lysed lipids containing biomass" insofar relates to a suspension which contains water, cell debris and oil as set free by the cells of the biomass, but beyond that may also comprise further components, in particular salts, intact cells, further contents of the lysed cells as well as components of a fermentation medium, in particular nutrients. In a preferred embodiment of the invention, only small amounts of intact cells, in particular less than 20%, preferably less than 10%, more preferably less than 5% (relating to the total number of intact cells as present before lysing the cells of the biomass) are present in the lysed biomass after the step of lysing the cells.

Lysing of the cells may be realized for example by utilizing a French cell press, sonicator, homogenizer, microfluidizer, ball mill, rod mill, pebble mill, bead mill, high pressure grinding roll, vertical shaft impactor, industrial blender, high shear mixer, paddle mixer, and/or polytron homogenizer.

In a preferred embodiment of the invention lysing of the cells is carried out without applying high mechanical stress on the cells. According to the invention, the energy input onto the cells in the lysing step preferably amounts to not more than 50 kWh per tonne of suspension, in particular not more than 40, 30 or 20 kWh per tonne of suspension, especially preferably not more than 15, 10 or 5 kWh per tonne of suspension.

In a preferred embodiment of the invention, lysing of the cells comprises an enzymatic treatment of the cells by applying a cell-wall degrading enzyme.

According to the invention, the cell-wall degrading enzyme is preferably selected from proteases, cellulases (e.g., Cellustar CL (Dyadic), Fibrezyme G2000 (Dyadic), Celluclast (Novozymes), Fungamyl (Novozymes), Viscozyme L (Novozymes)), hemicellulases, chitinases, pectinases (e.g., Pectinex (Novozymes)), sucrases, maltases, lactases, alpha-glucosidases, beta-glucosidases, amylases (e.g., Alphastar Plus (Dyadic); Termamyl (Novozymes)), lysozymes, neuraminidases, galactosidases, alpha-mannosidases, glucuronidases, hyaluronidases, pullulanases, glucocerebrosidases, galactosylceramidases, acetylgalactosaminidases, fucosidases, hexosaminidases, iduronidases, maltases-glucoamylases, xylanases (e.g., Xylanase Plus (Dyadic), Pentopan (Novozymes)), beta-glucanases (e.g., Vinoflow Max (Novozymes), Brewzyme LP (Dyadic)), mannanases, and combinations thereof. The protease may be selected from serine proteases, threonine proteases, cysteine proteases, aspartate proteases, metalloproteases, glutamic acid proteases, alcalases (subtilisins), and combinations thereof. The chitinase may be a chitotriosidase. The pectinase may be selected from pectolyases, pectozymes, polygalacturonases, and combinations thereof.

The adequate pH for utilizing the enzyme depends on the pH optimum of the enzyme. The pH optimum of the enzyme is known to those skilled in the art or otherwise can be determined easily.

In a preferred embodiment of the invention, an enzyme with a pH optimum of between 6.5 and 8.5, preferably of between 7.0 and 8.0, in particular of about 7.5, is used, so that the pH applied in this step is from 6.5 to 8.5, in particular from 7.0 to 8.0, preferably from 7.3 to 7.7. A preferred enzyme which can be used in this pH range is an alcalase.

The enzyme is preferably added as a concentrated enzyme solution, preferably in an amount of 0.01 to 1.5 wt.-%, more preferably in an amount of 0.03 to 1.0 wt.-%, above all in an amount of 0.05 to 0.5 wt.-%, relating to the amount of concentrated enzyme solution as added in relation to the total amount of the suspension after addition of the concentrated enzyme solution.

In a very preferred embodiment of the invention, lysing of the cells is carried out as follows:
a) Heating the suspension of (a) to a temperature of between 50° C. and 70° C., preferably to a temperature of between 55° C. and 65° C., and adding a cell wall-degrading enzyme to the fermentation broth, and adjusting an adequate pH value, if necessary, at which the enzyme is properly working;
b) Keeping the temperature and pH in the ranges as depicted in (b) for at least one hour, preferably for at least two hours, more preferably for two to four hours.

In step (a), the enzyme can be added before or after heating up the suspension and/or before or after adjusting the pH. In the same way heating up of the suspension can be carried out before or after adjusting the pH.—But in a preferred embodiment, the enzyme is added after heating up of the suspension and after adjusting the pH, if adjusting of the pH is necessary, at all.—In a very preferred embodiment all measures are carried out more or less simultaneously.

Preferably, in the steps (a) and (b) the suspension is continuously mixed by using a stirrer and/or an agitator.

In a further preferred embodiment of the invention, after lysing of the cells of the biomass and before the demulsification step, the suspension is concentrated to a total dry matter content of 30 to 60 wt.-%, more preferably 35 to 55 wt.-%, in particular 40 to 50 wt.-%.

Concentration of the suspension is preferably carried out by evaporation of water at a temperature not higher than 100° C., preferably 70° C. to 100° C., more preferably 80° C. to 90° C., until a total dry matter content of 30 to 60 wt.-% more preferably 35 to 55 wt.-%, in particular 40 to 50 wt.-%, is reached.

Concentration of the suspension is preferably carried out in a forced circulation evaporator (for example available from GEA, Germany) to allow fast removal of the water.

In general, adjusting the pH value can be carried out according to the invention by using either bases or acids as known to those skilled in the art. Decreasing of the pH can be carried out in particular by using organic or inorganic acids like sulfuric acid, nitric acid, phosphoric acid, boric acid, hydrochloric acid, hydrobromic acid, perchloric acid, hypochlorous acid, chlorous acid, fluorosulfuric acid, hexafluorophosphoric acid, acetic acid, citric acid, formic acid, or combinations thereof. As a high content of chloride is desirably avoided, in a preferred embodiment of the invention no or only small amounts of hydrochloric acid are used in the process of the current invention. According to the invention, sulfuric acid is the preferred substance for decreasing the pH value.—Increasing of the pH can be carried out in particular by using organic or inorganic bases like hydroxides, in particular sodium hydroxide, lithium hydroxide, potassium hydroxide, and/or calcium hydroxide, carbonates, in particular sodium carbonate, potassium carbonate, or magnesium carbonate, and/or bicarbonates, in particular lithium bicarbonate, sodium bicarbonate, and/or potassium bicarbonate.—Due to easiness of handling, the acids and bases are preferably used in liquid form, in particular as concentrated solutions. Thus, caustic soda is the preferred substance for increasing the pH value.

The method according to the invention preferably comprises as a further step the harvesting of the PUFAs containing lipid from the demulsified composition as obtained in step (d).

The harvesting of the PUFAs containing lipid preferably comprises neutralization of the demulsified suspension and subsequent separation of the thus obtained oil containing light phase from the water, salts, cell debris and residual oil containing heavy phase.

Neutralization of the demulsified composition is preferably realized by adding an acid, preferably sulfuric acid, to adjust a pH value of 5.5 to 8.5, in particular 6.5 to 8.5, preferably 7.0 to 8.0. Before starting separation of the light phase from the heavy phase the thus obtained neutralized composition may be stirred at said pH value from several minutes up to several hours.

Separation of the oil containing light phase from the water, salts and cell debris containing heavy phase is preferably realized by mechanical means and preferably at a temperature of 60-90° C., more preferably 70-80° C., and at a pH value of preferably 6-9, more preferably 7-8.5. "Mechanical means" refers in particular to filtration and centrifugation methods as known to those skilled in the art.

After separation of the oil containing light phase, the PUFAs containing oil thus obtained can further be worked up by applying methods as known to those skilled in the art, in particular refining, bleaching, deodorizing and/or winterizing.

A particular advantage of the method of the current invention is that it can be carried out without the use of any organic solvent, in particular without the use of any polar or non-polar organic solvent. Thus, in a preferred embodiment of the invention, no or only little amounts of organic solvents, in particular of polar or non-polar organic solvents, are used for isolating the PUFAs containing oil from the biomass. Typical organic solvents are hexane and ethanol.

In a preferred embodiment of the invention less than 2 wt.-% non-polar organic solvents are used, more preferably less than 1, 0.5 or 0.1 wt.-%. In a particularly preferred embodiment of the invention no non-polar organic solvent is used, at all. In a very preferred embodiment of the invention less than 2 wt.-% organic solvents are used, in general, particularly preferred less than 1, 0.5 or 0.1 wt.-%. In a particularly very preferred embodiment of the invention no organic solvents are used, at all, for isolating the PUFAs containing oil from the biomass.—This means in particular for this embodiment that the suspension as employed in the method according to the invention as well as all compositions as obtained by said single method steps preferably contain non-polar organic solvents, preferably organic solvents in general, in an amount of less than 2 wt.-%, more preferably less than 1 wt.-%, in particular less than 0.5 or 0.3 wt.-%, above all in an amount of less than 0.1 or 0.05 wt.-%.

A further advantage of the method of the current invention is that a very effective separation of the oil from the remaining biomass can be realized without the addition of sodium chloride, which is normally used for salting out the oil from the biomass. Preferably the method can be carried out without the addition of chloride salts, at all, above all without the addition of any salts for salting out the oil. But small amounts of chloride salts, in particular sodium chloride, might be present in the suspension due to the fermentation medium as used for growing of the biomass.

Thus, in a preferred embodiment of the current invention, no or only little amounts of sodium chloride are used for improving the oil isolation. In a preferred embodiment of the invention less than 1 wt.-% of sodium chloride, are used, more preferably less than 0.5 or 0.2 wt.-% of sodium chloride are used for isolating the oil from the biomass, above all less than 0.1 or 0.05 wt.-%, wherein the wt.-% relate to the total weight of the composition after addition of the sodium chloride.—This means in particular for this embodiment that the suspension as employed in the method according to the invention as well as all compositions as obtained by said single method steps preferably contain sodium chloride in an amount of less than 2 wt.-%, more preferably less than 1 wt.-%, in particular less than 0.5 or 0.3 wt.-%, above all in an amount of less than 0.1 or 0.05 wt.-%.

In a particularly preferred embodiment of the invention no or only little amounts of chloride salts are used for improving the oil isolation, at all. In this embodiment preferably less than 1 wt.-% of chloride salts, more preferably less than 0.5 or 0.2 wt.-% of chloride salts are used for isolating the oil from the biomass, above all less than 0.1 or 0.05 wt.-%, wherein the wt.-% relate to the total weight of the composition after addition of the chloride salts.—This means in particular for this embodiment that the suspension as employed in the method according to the invention as well as all compositions as obtained by said single method steps preferably contain chloride, in particular chloride salts, in an amount of less than 2 wt.-%, more preferably less than 1 wt.-%, in particular less than 0.5 or 0.3 wt.-%, above all in an amount of less than 0.1 or 0.05 wt.-%.

In a very preferred embodiment of the invention no or only little amounts of salts are used for improving the oil isolation, in general. In this embodiment preferably less than 1 wt.-% of salts, more preferably less than 0.5 or 0.2 wt.-% of salts are used for isolating the oil from the biomass, above all less than 0.1 or 0.05 wt.-%, wherein the wt.-% relate to the total weight of the composition after addition of the salts.—This means in particular for this embodiment that the suspension as employed in the method according to the invention as well as all compositions as obtained by said single method steps preferably contain salts in general in an amount of less than 2 wt.-%, more preferably less than 1 wt.-%, in particular less than 0.5 or 0.3 wt.-%, above all in an amount of less than 0.1 or 0.05 wt.-%.

The methods of the current invention allow a very effective separation of the oil contained in the biomass from the cell-debris and other substances as contained in the fermentation broth. By using the methods of the current invention preferably more than 80 wt.-%, in particular more than 90 wt.-% of the oil contained in the biomass can be separated from the biomass and isolated.

It turned out that the oil as obtained by applying the method of the current invention has some advantageous characteristics over the PUFAs containing oils as disclosed in the state of the art so far. In particular it exhibits very low oxidation values, a low content of free fatty acids and impurities, a very low viscosity and a very high flash point.

Thus, a further subject of the current invention is an oil as obtained or as obtainable by a method according to the current invention.

A further subject of the current invention is therefore also a PUFAs containing oil exhibiting the following characteristics: a) a peroxide value of less than 0.5, preferably less than 0.3, in particular less than 0.15; b) an anisidine value of less than 15, preferably less than 10; c) preferably a content of free fatty acids of less than 1 wt.-%; d) preferably a content of moisture and impurities of less than 1 wt.-%, preferably less than 0.5 wt.-%; e) preferably a viscosity of less than 250 cps, more preferably of less than 200 cps, in particular of less than 160 cps; e) preferably a flash point of at least 350° C., more preferably of at least 400° C., in particular of at least 450° C.; f) preferably a content of omega-3 fatty acids, in particular of DHA and EPA, of at least 35 wt.-%, preferably at least 40 or 45 wt.-%, above all at least 50 wt.-%; g) preferably DHA and EPA each in an amount of at least 8 wt.-%, preferably at least 10 wt.-%, above all at least 15 wt.-%; h) preferably an amount of organic solvents of less than 0.5 wt.-%, more preferably less than 0.1 wt.-%, in particular less than 0.05 wt.-%, above all less than 0.01 wt.-%; i) preferably an amount of chlorides of less than 0.1 wt.-%, more preferably less than 0.05 wt.-%, in particular less than 0.01 wt.-%; j) preferably a content of crude fat of more than 90 wt.-%.

The anisidine value (AV) is determined in accordance with AOCS Official Method Cd 18-90. The AV is a measure for secondary reaction products of the fatty acids, such as aldehydes and ketones, that occur during oxidation of the oil.

The peroxide value (PV) is determined in accordance with the AOCS Official Method CD 8-53. The PV is a measure for primary reaction products, such as peroxide and hydroperoxides, that occur during oxidation of the oil.—According to the invention the PV is measured in meq/kg.

The content of free fatty acids is determined in accordance with AOCS Official Method AOCS Ca 5a-40. The content of moisture is determined in accordance with AOCS Official Methods AOAC 930.15, 935.29. The content of insoluble impurities is determined in accordance with AOCS Official Method AOCS 3a-46. The amount of DHA and EPA is determined in accordance with AOCS Official Method AOCS Ce 1b-89. The amount of total fat is determined in accordance with AOCS Official Method AOCS 996.06. The amount of crude fat is determined in accordance with AOCS Official Methods AOAC 920.39, 954.02.

As the isolation of the oil is carried out by using no or only small amounts of solvents and by also using no or only small amounts of sodium chloride, the aqueous phase obtained as a by-product is preferably substantially free of organic solvents and sodium chloride, as well. Thus, the aqueous phase can be utilized in different ways, either directly after separation of the oil phase or after further work-up like concentrating and/or drying.

A further subject of the current invention is therefore a PUFAs containing aqueous suspension, containing a biomass, preferably a delipidated biomass, as obtained or as obtainable by a method according to the current invention. A further subject of the current invention is therefore also a concentrate or a dried product as obtained or obtainable by concentrating and/or drying this aqueous suspension. When concentrating the aqueous suspension, it is preferably dried until a total dry matter (TDM) content of 20 to 60 wt.-% is reached.—In the following the expression "aqueous suspension according to the invention" refers to the aqueous phase as obtained after separation of the oil phase as well as to any concentrated suspensions of this aqueous phase as obtained by concentrating of this aqueous phase. Drying is preferably carried out by solvent evaporation, as described further below.

A further subject of the current invention is therefore also a PUFAs containing aqueous suspension, containing a biomass, in particular cell debris of a delipidated biomass, characterized by a content of non-polar organic solvents of less than 1 wt.-%, preferably less than 0.5 or 0.2 wt.-%, more preferably less than 0.1 or 0.05 wt.-%, above all less than 0.01 wt.-%, and further characterized by a content of chloride ions of less than 1 wt.-%, preferably less than 0.5 or 0.2 wt.-%, more preferably less than 0.1 or 0.05 wt.-%.

A further subject of the current invention is therefore in particular also a PUFAs containing aqueous suspension, containing a biomass, in particular, cell debris of a delipidated biomass, characterized by a content of organic solvents of less than 1 wt.-%, preferably less than 0.5 or 0.2 wt.-%, more preferably less than 0.1 or 0.05 wt.-%, above all less than 0.01 wt.-%, and further characterized by a content of chloride ions of less than 1 wt.-%, preferably less than 0.5 or 0.2 wt.-%, more preferably less than 0.1 or 0.05 wt.-%.

A preferred subject of the current invention is therefore also a PUFAs containing aqueous suspension, containing a Thraustochytrid biomass, in particular cell debris of a delipidated Thraustochytrid biomass, characterized by a content of non-polar organic solvents of less than 1 wt.-%, preferably less than 0.5 or 0.2 wt.-%, more preferably less than 0.1 or 0.05 wt.-%, above all less than 0.01 wt.-%, and further characterized by a content of chloride ions of less than 1 wt.-%, preferably less than 0.5 or 0.2 wt.-%, more preferably less than 0.1 or 0.05 wt.-%.

A particularly preferred subject of the current invention is therefore also a PUFAs containing aqueous suspension, containing a Thraustochytrid biomass, in particular, cell debris of a delipidated Thraustochytrid biomass, characterized by a content of organic solvents of less than 1 wt.-%, preferably less than 0.5 or 0.2 wt.-%, more preferably less than 0.1 or 0.05 wt.-%, above all less than 0.01 wt.-%, and further characterized by a content of chloride ions of less than 1 wt.-%, preferably less than 0.5 or 0.2 wt.-%, more preferably less than 0.1 or 0.05 wt.-%.

The aqueous suspensions of the invention as described before preferably exhibit a total dry matter (TDM) content of 20 to 60 wt.-%, in particular of 25 to 55 wt.-%, more preferably of 30 to 50 wt.-%, as such concentrated suspensions turned out as particularly suitable for the applications of the invention as described below.

"Chloride" according to the invention refers to the amount of detectable chlorine. The amount of chlorine as present can be determined for example by elemental analysis according to DIN EN ISO 11885. The chlorine is present in the form of salts which are called "chlorides". The content of chloride as mentioned according to the invention—also called "chloride ions"—only refers to the amount of detectable chlorine, not to the amount of the complete chloride salt, which comprises besides the chloride ion also a cationic counterion.

In a particularly preferred embodiment of the current invention the water, salts, residual oil and cell debris containing aqueous phase, which is obtained as by-product in the oil harvesting step as described before, is converted into a dried biomass by drying the biomass to a total dry matter content of more than 90 wt.-%.

Thus, a further subject of the current invention is also a PUFAs containing biomass, in particular a delipidated PUFAs containing biomass, characterized by a content of non-polar organic solvents of less than 2 wt.-%, preferably less than 1, 0.5 or 0.2 wt.-%, more preferably less than 0.1, 0.05 or 0.02 wt.-% and further characterized by a content of chloride ions of less than 2 wt.-%, preferably less than 1, 0.5 or 0.2 wt.-%, more preferably less than 0.1 or 0.05 wt.-%.

Thus, a further subject of the current invention is also a PUFAs containing biomass, in particular a delipidated PUFAs containing biomass, characterized by a content of organic solvents of less than 2 wt.-%, preferably less than 1, 0.5 or 0.2 wt.-%, more preferably less than 0.1, 0.05 or 0.02 wt.-% and further characterized by a content of chloride ions of less than 2 wt.-%, preferably less than 1, 0.5 or 0.2 wt.-%, more preferably less than 0.1 or 0.05 wt.-%.

Thus, a preferred subject of the current invention is also a PUFAs containing Thraustocyhtrid biomass, in particular a delipidated Thraustochytrid biomass, characterized by a content of non-polar organic solvents of less than 2 wt.-%, preferably less than 1, 0.5 or 0.2 wt.-%, more preferably less than 0.1, 0.05 or 0.02 wt.-% and further characterized by a content of chloride ions of less than 2 wt.-%, preferably less than 1, 0.5 or 0.2 wt.-%, more preferably less than 0.1 or 0.05 wt.-%.

Thus, a particularly preferred subject of the current invention is also a PUFAs containing Thraustochytrid biomass, in particular a delipidated Thraustochytrid biomass, characterized by a content of organic solvents of less than 2 wt.-%, preferably less than 1, 0.5 or 0.2 wt.-%, more preferably less than 0.1, 0.05 or 0.02 wt.-% and further characterized by a content of chloride ions of less than 2 wt.-%, preferably less than 1, 0.5 or 0.2 wt.-%, more preferably less than 0.1 or 0.05 wt.-%.

As preferably the preparation is carried out without the use of non-polar organic solvents, preferably without the use of any organic solvents, at all, and without the use of sodium chloride, preferably without the use of chloride salts, at all, the resulting biomass is preferably free of any non-polar organic solvents, preferably free of any organic solvents, in general, and further essentially free of any chloride ions, at all, wherein "essentially free" means that it contains chloride ions in an amount of less than 0.1 wt.-%, in particular in an amount of less than 0.05 wt.-%.

The biomass according to the invention exhibits preferably a moisture content of not more than 10 wt.-%, preferably not more than 5 wt.-%.

The biomass thus obtained preferably comprises lipids (crude fat) in an amount of about 3 to 14 wt.-%, in particular about 4 to about 14 wt.-%, preferably in an amount of about 4.5 to about 12 wt.-%, more preferably in an amount of about 5 to about 10 wt.-%. Further, the lipid preferably comprises at least one PUFA selected from DHA and EPA, more preferably a mixture of DHA and EPA, wherein the ratio of DHA to EPA is preferably between 3:2 to 4:1 and wherein the amount of DHA is preferably from 30 to 50 wt.-% of the total amount of lipids contained and the amount of EPA is preferably from 10 to 20 wt.-%. of the total amount of lipids contained. Accordingly, also the aqueous suspensions as described before are preferably characterized by being convertible by drying into a biomass with such a crude fat content and/or EPA content and/or DHA content by drying the aqueous suspension to a moisture content of not more than 10 wt.-%, preferably not more than 5 wt.-%.

The biomass preferably further comprises amino acids in an amount of 15 to 25 wt.-%, more preferably in an amount of 17 to 23 wt.-%, and exhibits preferably a crude protein content of 25 to 35 wt.-%. Accordingly, also the aqueous suspensions as described before are preferably characterized by being convertible by drying into a biomass with such an amino acid and/or crude protein content by drying the aqueous suspension to a moisture content of not more than 10 wt.-%, preferably not more than 5 wt.-%.

The biomass preferably further exhibits a crude fiber content of less than 5 wt.-%, preferably less than 2 wt.-%, more preferably of about 0 wt.-%. Accordingly, also the aqueous suspensions as described before are preferably characterized by being convertible by drying into a biomass with such a crude fiber content by drying the aqueous suspension to a moisture content of not more than 10 wt.-%, preferably not more than 5 wt.-%.

The dried biomass is preferably a delipidated biomass, that means a biomass, of which the major part of the lipids have been removed, preferably by a process as disclosed in this application. As the separation of oil from the biomass is very effectively, the remaining oil in the biomass is preferably less than 20 wt.-%, preferably less than 15 wt.-%, more preferably less than 10 wt.-%, of the oil as originally contained in the biomass. But as the oil cannot be removed completely by such a process, a substantial amount of oil is still contained also in the delipidated biomass according to the invention. That means that the term "delipidated biomass" according to the invention refers to a lysed biomass, from which the major part of oil has been removed, preferably by a process or method as disclosed in this application, but which still contains a substantial part of lipids, in particular of PUFAs containing lipids, wherein the amount of lipids in the dried delipidated biomass is preferably from 3-14 wt.-%, in particular 4-14 wt.-%, preferably from 4.5-12 wt.-%, more preferably from 5-10 wt.-%. Thus, the "delipidated biomass" according to the invention might also be called a "partially delipidated biomass" or a "substantially delipidated biomass".

Thus, a further subject of the current invention is a method of obtaining a biomass which is substantially free of non-polar organic solvents, preferably free of organic solvents, in general, and which is further substantially free of sodium chloride, preferably free of chloride salts, in general, comprising the method steps as mentioned before.

Conversion of the water, salts, remaining oil and cell debris containing heavy phase, which is obtained as by-product in the oil harvesting step, into a dried biomass by drying the biomass to a total dry matter content of more than 90 wt.-%, can be carried out in different ways.

In a very preferred way, the transformation is carried out by concentration of the heavy phase to a dry matter content of 30-50 wt.-%, preferably 35-45 wt.-%, and subsequent spray granulation of the biomass by means of fluidized bed granulation. By doing that, in a very efficient way, a biomass with advantageous features can be obtained. Spray granulation by means of fluidized bed granulation is disclosed in more detail in EP13176661.0.

The biomass as obtained in that way has some further advantageous characteristics as follows: it has a good flowability (preferably at least grade 4), a low dust value (preferably free of dust), a high bulk density of preferably more than 500 kg/m3, and/or a high energy value of at least 3500 kcal/kg, preferably of about 3800 to 4200 kcal/kg.

Concentration of the heavy phase to a dry matter content of 30-50 wt.-% is preferably carried out by solvent evaporation, in particular vacuum evaporation, and/or by using a rotary evaporator, a thin-film evaporator or a falling-film evaporator. A useful alternative to solvent evaporation is reverse osmosis.

For determining the flowability of the granular biomass conical glass efflux vessels with different size outflow openings are used (Klein: Seifen, Öle, Fette, Wachse 94, 12 (1968)). The glass vessels exhibit a height of 70 mm, a maximal inner diameter of 36 mm, a maximal outer diameter of 40 mm and circular apertures at the conical end of the glass vessels with diameters as follows: 2.5; 5; 8; 12;18 mm. The glass vessels are completely filled with the granular biomass and subsequently fixed in a rack with the aperture directed downwards. Preferably, the aperture of the glass vessels is opened by removing a covering located on the aperture after having fixed the glass vessels on the rack.

The flowability is determined as follows: If the granular material can flow out of the vessel with the smallest diameter (2.5 mm) without stagnation, then the flowability is determined as 1; if it can flow out of the vessel with diameter of 5 mm without stagnation, then the flowability is determined as 2; and so on. A flowability of 6 means that the granular material can not flow out of the vessel with the broadest diameter (18 mm), at all, or it can flow out of this vessel only with stagnation.—Thus, a flowability of 4 means that the granular material can flow out of the vessel with a diameter of 12 mm without stagnation.

"Dust-free" according to the invention is understood to mean a powder which contains only low fractions (<10% by weight, preferably <5% by weight, in particular <3% by weight, especially <1% by weight) of particle sizes below 100 micrometres.

In a preferred embodiment of the invention, a fraction of at least 80% by weight, in particular at least 90% by weight, particularly preferably at least 95% by weight, especially at least 98% by weight of the particles of the biomass possess a particle size of from 100 to 2500 micrometres, preferably 300 to 2500 micrometres, in particular 500 to 2200 micrometres, more preferably 1000 to 2000 micrometers.

The mean particle diameter d50 of the particles of the biomass is preferably in the range of 500 to 2200 micrometers, more preferably in the range of 1000 to 2000 micrometers, in particular in the range of 1300 to 1900 micrometers.

Grain or particle size is preferably determined according to the invention by laser diffraction spectrometric methods. Possible methods are described in the text book "Teilchengrößenmessung in der Laborpraxis" [Particle size measurement in the laboratory] by R. H. Müller and R. Schuhmann, Wissenschaftliche Verlagsgesellschaft Stuttgart (1996) and in the text book "Introduction to Particle Technology" by M. Rhodes, Wiley & Sons (1998). Inasmuch as various methods can be used, the first-cited usable method from the text book of R.H. Müller and R. Schuhmann for the measuring of particle size is preferably used.

The bulk density of the biomass according to the invention is preferably 400 to 800 kg/m$^3$, particularly preferably 450 to 750 kg/m$^3$, in particular 500 to 750 kg/m$^3$.

As alternative to the spray-granulation other drying methods, in particular other convective drying methods, like tunnel drying or spray drying, in particular nozzle spray drying, or contact drying methods, like drum drying, or radiation drying methods, like infrared drying, of the concentrated heavy phase would be applicable alternatives, wherein by using those methods normally particles with a smaller or bigger diameter are obtained.

According to the invention, during the drying process, an anti-caking agent, in particular silica, preferably a hydrophobic or hydrophilic silica, may optionally be added to the biomass to prevent caking. For this purpose, the fermentation broth comprising biomass as well as the silica are preferably sprayed into the particular drying zone. Alternatively or additionally, the biomass may be mixed with the anti-caking agent after the drying process. With respect to the use of silica as anti-caking agent reference is made in particular to the patent application EP13187631.0.

In a particular embodiment, the biomass according to the invention has a concentration of an anti-caking agent, in particular silica, preferably hydrophilic or hydrophobic silica, of 0.2 to 10% by weight, in particular 0.5 to 7% by weight, especially 0.5 to 5% by weight.

Conversion of a fine-grained powder into a coarse-grained dust-free product can be realized by granulating processes. Conventional organic or inorganic auxiliaries or supports such as starch, gelatin, cellulose derivatives or similar substances, which are typically used in food processing or feed processing as binding agents, gelling agents or thickeners, may optionally be used in this subsequent granulation process. Further auxiliaries that are preferably used according to the invention are disclosed in WO 2016/050560, with carboxymethylcellulose being a particulary preferred binding agent.

Thus, in a particular embodiment of the current invention, the biomass contains an agglomeration auxiliary, in particular a modified polysaccharide, preferably carboxymethylcellulose, in an amount of from 0.05 to 10 wt.-%, preferably in an amount of 0.1 to 5 wt.-%.

A product having the desired particle size and/or particle size distribution can optionally be obtained from the granulate as obtained by drying and/or granulation by subsequent sieving or dust separation.

After drying and optionally granulating and/or sieving of the biomass, the dried biomass is preferably stored or packed.

The particulate biomass of the invention as well as the aqueous suspensions of the invention can be used in different ways. For example, they can be used in order to produce a foodstuff or feedstuff, as the biomass and aqueous suspensions according to the invention surprisingly turned out to be well accepted as feed ingredient by animals, in particular by beef cattle. Alternatively they may be used directly as foodstuff or feedstuff.

A feedstuff or foodstuff comprising a particulate biomass or an aqueous suspension according to the invention is therefore a further subject matter of the present invention. The feedstuff may for example be used for feeding poultry, swine, minks, ruminants, in particular beef cattle or calves, sheep, goats, companion animals or animals hold in aquaculture. In a very preferred embodiment of the invention, the feedstuff is used for feeding beef cattle. The feedstuff or foodstuff preferably comprises the biomass in an amount of 2 to 60 wt.-%, preferably in an amount of 5 to 50 wt.-%, more preferably in an amount of 10 to 30 wt.-%.

A further subject matter of the present invention is therefore likewise the use of a particulate biomass and/or of an aqueous suspension according to the invention for producing a foodstuff or feedstuff.

A further subject matter of the present invention is therefore likewise a method for producing a feedstuff or foodstuff, in which a particulate biomass and/or an aqueous suspension according to the invention is used, and is preferably mixed with further feedstuff or foodstuff ingredients.

In a preferred embodiment of the invention, the particulate biomass and/or the aqueous suspension is used for producing a foodstuff or feedstuff, in which the biomass and/or the aqueous suspension is preferably mixed with other foodstuff or feedstuff ingredients and is then processed to give the foodstuff or feedstuff.

The mixture of biomass and/or aqueous suspension and other foodstuff or feedstuff ingredients is processed in a preferred embodiment by an extrusion process, in order to obtain portions of foodstuff or feedstuff ready for sale. Alternatively, a pelleting method may also be used.

A screw or twin-screw extruder is preferably employed in the extrusion process. The extrusion process is preferably carried out at a temperature of 80-220° C., particularly 100-190° C., a pressure of 10-40 Bar, and a shaft rotational speed of 100-1000 rpm, particularly 300-700 rpm. The residence time of the mixture introduced is preferably 5-30 seconds, in particular 10-20 seconds.

In a mode of the extrusion process which is preferred in accordance with the invention, the process comprises a compacting step and a compression step.

It is preferred to intimately mix the components with each other before carrying out the extrusion process. This is preferably carried out in a drum equipped with vanes. In this mixing step, a preferred embodiment includes an injection of steam, in particular so as to bring about the swelling of the starch which is preferably present.

Before being mixed with the biomass and/or aqueous suspension, the further foodstuff or feedstuff ingredients are preferably comminuted—if required—so as to ensure that a homogeneous mixture is obtained in the mixing step. The comminuting of the further foodstuff or feedstuff ingredients may be carried out, for example, using a hammer mill.

A further subject of the current invention is therefore a method of feeding animals, wherein a particulate biomass and/or an aqueous suspension according to the invention are provided to animals, preferably after mixing the particulate biomass and/or the aqueous suspension with further feedstuff ingredients, wherein the animals are preferably selected from poultry, swine, minks, ruminants, in particular from calves and beef cattle, sheep, goats, companion animals or animals hold in aquaculture.

Alternatively the biomass and/or aqueous suspension according to the invention may be used in land applications, in particular as (organic) fertilizer, NPC (nitrogen/phosphorous/potassium source), soil enhancer, plant enhancer and/or composting aid, for producing biogas, for wastewater treatment or as alternative fuel, in particular for cement kilns. It might be further used as part of a fermentation medium for producing microorganisms, in particular for producing further PUFAs containing biomass.

A further subject of the current invention is therefore a method for enhancing soil, wherein a particulate biomass and/or an aqueous suspension according to the invention are strewed on and possibly mixed with ground, in particular with farmland soil or garden soil.

A further subject of the current invention is therefore also a method for fertilizing and/or composting ground, in particular farmland or garden, wherein a particulate biomass and/or an aqueous suspension according to the invention are strewed on and possibly mixed with ground, in particular with farmland soil or garden soil.

A further subject of the current invention is therefore also a method for producing biogas, wherein a particulate biomass and/or an aqueous suspension according to the invention is subjected to microbial degradation under anaerobic conditions, in particular by making use of methanogenic bacteria.

A further subject of the current invention is therefore also a method for treatment of wastewater, wherein wastewater is mixed with a particulate biomass and/or an aqueous suspension according to the invention.

A further subject of the current invention is therefore also a method for producing microorganisms, in particular for producing a PUFAs containing biomass, wherein a particulate biomass and/or aqueous suspension according to the invention is used as part of the fermentation medium.

The method according to the invention may further comprise as a pretreatment step the pasteurization of the suspension of the biomass, before carrying out the lysis of the cells. The pasteurization is preferably carried out for 5 to 80 minutes, in particular 20 to 60 minutes, at a temperature of 50 to 121° C., in particular 50 to 70° C.

The PUFAs containing cells of the biomass are preferably microbial cells or plant cells. Preferably, the cells are capable of producing the PUFAs due to a polyketide synthase system. The polyketide synthase system may be an endogenous one or, due to genetic engineering, an exogenous one.

Accordingly, "delipidated biomass" according to the invention in particular refers to the residues of such a PUFAs containing cells comprising biomass, in particular as disclosed further below, after having been subjected to an oil isolation process, in particular as disclosed further before.

The plant cells may in particular be selected from cells of the families Brassicaceae, Elaeagnaceae and Fabaceae. The cells of the family Brassicaceae may be selected from the genus *Brassica*, in particular from oilseed rape, turnip rape and Indian mustard; the cells of the family Elaeagnaceae may be selected from the genus *Elaeagnus*, in particular from the species *Oleae europaea*; the cells of the family Fabaceae may be selected from the genus *Glycine*, in particular from the species *Glycine max*.

The microbial organisms which contain a PUFAs containing lipid are described extensively in the prior art. The cells used may, in this context, in particular be cells which already naturally produce PUFAs (polyunsaturated fatty acids); however, they may also be cells which, as the result of suitable genetic engineering methods or due to random mutagenesis, show an improved production of PUFAs or have been made capable of producing PUFAs, at all. The production of the PUFAs may be auxotrophic, mixotrophic or heterotrophic.

The biomass preferably comprises cells which produce PUFAs heterotrophically. The cells according to the invention are preferably selected from algae, fungi, particularly yeasts, bacteria, or protists. The cells are more preferably microbial algae or fungi.

Suitable cells of oil-producing yeasts are, in particular, strains of Yarrowia, Candida, Rhodotorula, Rhodosporidium, Cryptococcus, Trichosporon and Lipomyces.

Suitable cells of oil-producing microalgae and algae-like microorganisms are, in particular, microorganisms selected from the phylum Stramenopiles (also called Heterokonta). The microorganisms of the phylum Stramenopiles may in particular be selected from the following groups of microorganisms: Hamatores, Proteromonads, Opalines, Developayella, Diplophrys, Labrinthulids, Thraustochytrids, Biosecids, Oomycetes, Hypochytridiomycetes, Commation, Reticulosphaera, Pelagomonas, Pelagococcus, Ollicola, Aureococcus, Parmales, Diatoms, Xanthophytes, Phaeophytes (brown algae), Eustigmatophytes, Raphidophytes, Synurids, Axodines (including Rhizochromulinales, Pedinellales, Dictyochales), Chrysomeridales, Sarcinochrysidales, Hydrurales, Hibberdiales, and Chromulinales. Other preferred groups of microalgae include the members of the green algae and dinoflagellates, including members of the genus *Crypthecodiurn*.

The biomass according to the invention preferably comprises cells, and preferably consists essentially of such cells, of the taxon Labyrinthulomycetes (Labyrinthulea, net slime fungi, slime nets), in particular those from the family of Thraustochytriaceae. The family of the Thraustochytriaceae (Thraustochytrids) includes the genera Althomia, Aplanochytrium, Aurantiochytrium, Botryochytrium, Elnia, Japonochytrium, Oblongichytrium, Parietichytrium, Schizochytrium, Sicyoidochytrium, Thraustochytrium, and Ulkenia. The biomass particularly preferably comprises cells from the genera Aurantiochytrium, Oblongichytrium, Schizochytrium, or Thraustochytrium, above all from the genus *Schizochytrium*.

In accordance with the invention, the polyunsaturated fatty acid (PUFA) is preferably a highly-unsaturated fatty acid (HUFA).

The cells present in the biomass are preferably distinguished by the fact that they contain at least 20% by weight, preferably at least 30% by weight, in particular at least 35% by weight, of PUFAs, in each case based on cell dry matter.

According to the current invention, the term "lipid" includes phospholipids; free fatty acids; esters of fatty acids; triacylglycerols; sterols and sterol esters; carotenoids; xanthophylls (e. g., oxycarotenoids); hydrocarbons; isoprenoid-derived compounds and other lipids known to one of ordinary skill in the art.—The terms "lipid" and "oil" are used interchangeably according to the invention.

In a preferred embodiment, the majority of the lipids in this case is present in the form of triglycerides, with preferably at least 50% by weight, in particular at least 75% by weight and, in an especially preferred embodiment, at least 90% by weight of the lipids present in the cell being present in the form of triglycerides.

According to the invention, polyunsaturated fatty acids (PUFAs) are understood to mean fatty acids having at least two, particularly at least three, C-C double bonds. According to the invention, highly-unsaturated fatty acids (HUFAs) are preferred among the PUFAs. According to the invention, HUFAs are understood to mean fatty acids having at least four C-C double bonds.

The PUFAs may be present in the cell in free form or in bound form. Examples of the presence in bound form are phospholipids and esters of the PUFAs, in particular monoacyl-, diacyl- and triacylglycerides. In a preferred embodiment, the majority of the PUFAs is present in the form of triglycerides, with preferably at least 50% by weight, in particular at least 75% by weight and, in an especially preferred embodiment, at least 90% by weight of the PUFAs present in the cell being present in the form of triglycerides.

Preferred PUFAs are omega-3 fatty acids and omega-6 fatty acids, with omega-3 fatty acids being especially preferred. Preferred omega-3 fatty acids here are the eicosapentaenoic acid (EPA, 20:5ω-3), particularly the (5Z,8Z,11Z,14Z,17Z)-eicosa-5,8,11,14,17-pentaenoic acid, and the docosahexaenoic acid (DHA, 22:6ω-3), particularly the (4Z,7Z,10Z,13Z,16Z,19Z)-docosa-4,7,10,13,16,19-hexaenoic acid.

In a very preferred embodiment of the current invention, cells, in particular a *Schizochytrium* strain, is employed which produces a significant amount of EPA and DHA, simultaneously, wherein DHA is preferably produced in an amount of at least 20 wt.-%, preferably in an amount of at least 30 wt.-%, in particular in an amount of 30 to 50 wt.-%, and EPA is produced in an amount of at least 5 wt.-%, preferably in an amount of at least 10 wt.-%, in particular in an amount of 10 to 20 wt.-% (in relation to the total amount of lipid as contained in the cells, respectively). DHA and EPA producing *Schizochytrium* strains can be obtained by consecutive mutagenesis followed by suitable selection of mutant strains which demonstrate superior EPA and DHA production and a specific EPA:DHA ratio. Any chemical or nonchemical (e.g. ultraviolet (UV) radiation) agent capable of inducing genetic change to the yeast cell can be used as the mutagen. These agents can be used alone or in combination with one another, and the chemical agents can be used neat or with a solvent.

Preferred species of microorganisms of the genus *Schizochytrium*, which produce EPA and DHA simultaneously in significant amounts, as mentioned before, are deposited under ATCC Accession No. PTA-10208, PTA-10209, PTA-10210, or PTA-10211, PTA-10212, PTA-10213, PTA-10214, PTA-10215.

The suspension of biomass according to the present invention, from which the PUFAs containing lipid is obtainable, is preferably a fermentation broth, in particular a fermentation broth with a biomass density of at least 80 or 100 g/l, preferably at least 120 or 140 g/l, more preferably at least 160 or 180 g/l (calculated as dry-matter content). Thus, the suspension may be obtained by culturing and growing suitable cells in a fermentation medium under conditions whereby the PUFAs are produced by the microorganism.

Methods for producing the biomass, in particular a biomass which comprises cells containing lipids, in particular PUFAs, particularly of the order Thraustochytriales, are described in detail in the prior art (see e.g. WO91/07498, WO94/08467, WO97/37032, WO97/36996, WO01/54510). As a rule, the production takes place by cells being cultured in a fermenter in the presence of a carbon source and of a nitrogen source, along with a number of additional substances like minerals that allow growth of the microorganisms and production of the PUFAs. In this context, biomass densities of more than 100 grams per litre and production rates of more than 0.5 gram of lipid per litre per hour may be attained.

The process is preferably carried out in what is known as a fed-batch process, i.e. the carbon and nitrogen sources are fed in incrementally during the fermentation. When the desired biomass has been obtained, lipid production may be induced by various measures, for example by limiting the nitrogen source, the carbon source or the oxygen content or combinations of these.

In a preferred embodiment of the current invention, the cells are grown until they reach a biomass density of at least 80 or 100 g/l, more preferably at least 120 or 140 g/l, in particular at least 160 or 180 g/l (calculated as dry-matter content). Such processes are for example disclosed in U.S. Pat. No. 7,732,170.

Preferably, the cells are fermented in a medium with low salinity, in particular so as to avoid corrosion. This can be achieved by using chlorine-free sodium salts as the sodium source instead of sodium chloride, such as, for example, sodium sulphate, sodium carbonate, sodium hydrogen carbonate or soda ash. Preferably, chloride is used in the fermentation in amounts of less than 3 g/l, in particular less than 500 mg/l, especially preferably less than 100 mg/l.

Suitable carbon sources are both alcoholic and non-alcoholic carbon sources. Examples of alcoholic carbon sources are methanol, ethanol and isopropanol. Examples of non-alcoholic carbon sources are fructose, glucose, sucrose, molasses, starch and corn syrup.

Suitable nitrogen sources are both inorganic and organic nitrogen sources. Examples of inorganic nitrogen sources are nitrates and ammonium salts, in particular ammonium sulphate and ammonium hydroxide. Examples of organic nitrogen sources are amino acids, in particular glutamate, and urea.

In addition, inorganic or organic phosphorus compounds and/or known growth-stimulating substances such as, for example, yeast extract or corn steep liquor, may also be added so as to have a positive effect on the fermentation.

The cells are preferably fermented at a pH of 3 to 11, in particular 4 to 10, and preferably at a temperature of at least 20° C., in particular 20 to 40° C., especially preferably at least 30° C. A typical fermentation process takes up to approximately 100 hours.

After the fermentation has ended, the cells may be pasteurized in order to kill the cells and to deactivate enzymes which might promote lipid degradation. The pasteurization is preferably effected by heating the biomass to a temperature of 50 to 121° C., preferably 50 to 70° C., for a period of 5 to 80 minutes, in particular 20 to 60 minutes.

Likewise, after the fermentation is ended, antioxidants may be added in order to protect the PUFAs present in the biomass from oxidative degradation. Preferred antioxidants in this context are BHT, BHA, TBHA, ethoxyquin, beta-carotene, vitamin E, in particular tocopherol, and vitamin C. The antioxidant, if used, is preferably added in an amount of 0.001 to 0.1 wt.-%, preferably in an amount of 0.002 to 0.05 wt.-%, relating to the total amount of the fermentation broth after addition of the antioxidant.

WORKING EXAMPLES

Example 1

An unwashed cell broth containing microbial cells (*Schizochytrium* sp.) at a biomass density of over 100 g/l was heated to 60° C. in an agitated vessel. After heating up the suspension, the pH was adjusted to 7.5 by using caustic soda (50 wt.-% NaOH solution), before an alcalase (Alcalase® 2.4 FG (Novozymes)) was added in liquid form in an amount of 0.5 wt.-% (by weight broth). Stirring was continued for 3 hours at 60° C. After that, the lysed cell mixture was transferred into a forced circulation evaporator (obtained from GEA, Germany) and heated to a temperature of 85° C. The mixture was concentrated in the forced circulation evaporator, until a total dry matter content of about 30 wt.-% was reached. The concentrated lysed cell mixture was transferred into a new vessel, heated up to 90° C. under low shear agitation, while adjusting the pH to 10.5 by adding caustic soda. Low shear agitation was continued for about 30 hours, while keeping the temperature at 90° C. and the pH above 9.0 by adding caustic soda.

After that the resulting demulsified mixture was neutralized by adding sulfuric acid to adjust a pH of 7.5. Phase separation into a light phase, containing the oil, and a heavy phase, containing water, cell-debris, residual oil and salts, was carried out mechanically by using a disc stack separator (Alfa Laval Disc Stack Centrifuge, LAPX 404/Clara 20)

After separation of the crude oil, the remaining cell debris were resuspended in the aqueous phase, concentrated and dried by spraygranulation.

Due to the efficient demulsification, more than 90 wt.-% of the oil could be separated from the biomass without the addition of organic solvents or sodium chloride.

The remaining heavy phase was converted into a solid biomass by concentrating via evaporation to a total dry matter of 45 wt.-% at a temperature of about 90° C. and subsequent drying via spray granulation in a fluidized bed spray granulator. The resulting biomass exhibits a high bulk density of more than 530 kg/m3, a high energy value of about 4000 kcal/kg and very good handling properties, in particular a flowability of 4. Comparable biomasses originating from Schyzochitria as available on the market exhibit all a much worse flowability of 6 and a much lower bulk density of between 325 to 500 kg/m3.

The invention claimed is:

1. A method of separating a polyunsaturated fatty acids (PUFAs)-containing lipid from the debris of a biomass, comprising the following steps:
 a) providing a suspension of a biomass comprising cells which contain a PUFAs-containing lipid;
 b) lysing the cells of the biomass;
 c) heating the suspension obtained in step b) to a temperature of 80° C. to 100° C., and adjusting the pH to a value of 9.0 to 11.5;
 d) maintaining the temperature and pH value in the ranges of paragraph c) for at least 10 hours thereby forming a demulsified suspension;
 e) harvesting the PUFAs-containing oil by:
  i) adding an acid to the demulsified suspension to adjust it to a pH of 5.5 to 8.5;
  ii) subsequently separating the resulting oil-containing light phase from the water, salt and cell debris-containing heavy phase;

wherein:
 after lysing cells in step b), and prior to steps c) and d), the suspension is concentrated to a total dry matter content of 30 to 60 wt.-% by evaporation of water;
 more than 90 wt.-% of the oil contained in the initial biomass is separated and isolated;
 the method is carried out without the addition of any salts for salting out the oil.

2. The method of claim 1, wherein, in step c) the suspension of lysed cells obtained in step b) is heated to a temperature of 85° C. to 95° C., and the pH is adjusted to a value of 9.0 to 11.0 and in step d), the temperature and pH are maintained for a period of 20 to 36 hours.

3. The method of claim 1, comprising as a further step the conversion of the water, salt, residual oil and cell debris containing heavy phase into a dried biomass with a total dry matter content of more than 90 wt.-%.

4. The method of claim 3, wherein conversion into a dried biomass is carried out by concentrating the heavy phase to a dry matter content of 30-50 wt.-% and subsequently spray granulating using a fluidized bed granulator.

5. The method of claim 1, wherein the suspension is provided as a fermentation broth with a biomass density of at least 80 g/l.

6. The method of claim 5, wherein the cells are selected from algae, fungi, protists, bacteria, microalgae, plant cells, and mixtures thereof.

7. The method of claim 5 wherein the cells are of the genus *Schizochytrium*.

8. The method of claim 4, wherein the suspension is provided as a fermentation broth with a biomass density of at least 80 g/l.

9. The method of claim 8, wherein the cells are selected from algae, fungi, protists, bacteria, microalgae, plant cells, and mixtures thereof.

10. The method of claim 8, wherein the cells are of the genus *Schizochytrium*.

11. The method of claim 1, wherein separation of step e)ii) is by filtration or centrifugation.

12. The method of claim 1, wherein, the suspension is concentrated to a total dry matter content of preferably 35 to 55 wt.-% by evaporation of water at a temperature not higher than 100° C.

13. The method of claim 12, wherein said temperature is 80° C. to 90° C.

* * * * *